United States Patent [19] [11] 4,148,823
Dubois [45] Apr. 10, 1979

[54] PROCESS FOR PREPARING p-ARYLAMINOPHENOLS WITH ALUMINUM SULFATE OR CARBOXYLATE

[75] Inventor: David R. Dubois, Kingsport, Tenn.

[73] Assignee: Eastman Kodak Company, Rochester, N.Y.

[21] Appl. No.: 914,715

[22] Filed: Jun. 12, 1978

[51] Int. Cl.$^2$ ............................................. C07C 89/00
[52] U.S. Cl. .................................................... 260/571
[58] Field of Search ..................... 260/571; 252/431 C, 252/440

[56] References Cited

U.S. PATENT DOCUMENTS

| | | | |
|---|---|---|---|
| 2,238,320 | 4/1941 | Hardman | 260/571 X |
| 2,780,647 | 2/1957 | Spiegler | 260/571 |
| 3,081,348 | 3/1963 | Spacht | 260/576 |
| 3,170,956 | 2/1965 | Olin | 260/576 |
| 3,794,668 | 2/1974 | Larkins, Jr. | 252/440 X |

Primary Examiner—Allen B. Curtis
Attorney, Agent, or Firm—J. Frederick Thomsen; Daniel B. Reece, III

[57] ABSTRACT

Process for the preparation of a p-arylaminophenol by reacting hydroquinone with a primary arylamino in the presence of a catalytic amount of aluminum sulfate or an aluminum lower carboxylate.

3 Claims, No Drawings

PROCESS FOR PREPARING P-ARYLAMINOPHENOLS WITH ALUMINUM SULFATE OR CARBOXYLATE

This invention concerns a novel process for the synthesis of p-arylaminophenols by the reaction of hydroquinone with a primary arylamine in the presence of aluminum sulfate or an aluminum carboxylate.

It is known that certain metal chlorides such as aluminum chloride, zinc chloride, and, especially, ferric chloride, can be used to catalyze the reaction of hydroquinone and primary arylamines to yield p-arylaminophenols. See U.S. Pat. No. 2,156,793. The use of iron and iron oxides in combination with an amine hydrochloride in a similar reaction to produce N,N'-diarylphenylenediamines is described in U.S. Pat. No. 3,081,348. The synthesis of arylaminonaphthalenes by the reaction of a naphthol and an arylamine in the presence of a silica-alumina type catalyst is described in U.S. Pat. No. 3,170,956.

In an effort to develop a commercially feasible process for the manufacture of p-arylaminophenols, specifically p-hydroxydiphenylamine, a silica-alumina type cracking catalyst, ferric chloride and aluminum chloride were tried as catalysts for the reaction of hydroquinone and aniline. The silica-alumina was unsatisfactory for a number of reasons. Relatively large amounts and higher reaction temperatures were necessary to obtain satisfactory yields. Also, since silica-alumina is not soluble in the reaction mixture, its use in the quantities required would present problems relative to its removal from the reactor after a production run. The use of ferric chloride also was unsatisfactory because it caused formation of larger amounts of the undesired diamine by-product, N,N'-diphenyl-p-phenylenediamine. Both ferric chloride and aluminum chloride cause aniline hydrochloride to sublime and condense on the surface of the condenser used in carrying out the reaction. This would cause serious difficulties in production equipment. To avoid the formation of aniline hydrochloride, ferric sulfate was tried but it gave an unacceptable conversion (23%) to product. Other catalysts, such as boric acid, aluminum isopropoxide, sodium methoxide and tetraisopropyl titanate, were tried with poor results.

It was then found that aluminum sulfate and aluminum acetate were excellent catalysts for preparing p-hydroxydiphenylamines by the reaction of hydroquinone and aniline. Both of those aluminum compounds give good yield of desired product with minimum formation of diamine byproduct. Furthermore, their use avoids the problem of aniline hydrochloride formation. Finding that aluminum sulfate and aluminum acetate were effective catalysts was unexpected since the relatively non-acidic sulfate and acetate salts of metals have not been known to be effective catalysts for this type of reaction.

My novel process, therefore, comprises reacting hydroquinone with a primary arylamine in the presence of a catalytic amount of aluminum sulfate or an aluminum lower carboxylate. The primary arylamine can be unsubstituted phenyl- and naphthyl-amine, or phenyl- and naphthyl-amines bearing substituents inert to or unaffected by the process conditions. Preferably, the arylamine is one having the formula

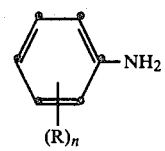

wherein R is lower alkyl or lower alkoxy and n is 0, 1 or 2. The term "lower" designates a carbon content of up to about 4 carbon atoms and thus typical groups represented by R include methyl, ethyl, butyl, methoxy, ethoxy and butoxy.

The temperature at which my novel process can be carried out is in the range of about 170° to 220° C. Lower temperatures result in poor conversions to the desired product, whereas temperatures significantly above 220° C. cause increased formation of diamine by-product. Best results are obtained using a temperature in the range of about 170° to 195° C. During the practice of the process, the water of reaction formed is removed as an azeotrope. Examples of some suitable azeotrope formers include benzene, toluene, xylene and aniline. The mole ratio of reactants can be varied substantially although the use of excess aniline is preferred to maximize conversion of hydroquinone.

The catalytically-effective amount of aluminum sulfate or aluminum lower carboxylate generally is in the range of about 0.10 to 0.50 weight percent, based on the hydroquinone and calculated as aluminum. The preferred amount of aluminum catalyst is about 0.12 to 0.30, calculated on the same basis. The aluminum lower carboxylate is a salt of aluminum and a lower ($C_1$-$C_4$) carboxylic acid such as acetic acid.

The products obtained from the process of my invention are used as chemical intermediates, for example, in the manufacture of dyes.

The practice of the process is further illustrated by the following examples.

EXAMPLE 1

Preparation: Hydroquinone (110 g., 1.0 mole), aniline (100 g., 1.07 moles), aluminum sulfate (1.9 g.), and xylene (10 ml.) were charged to a 500 ml. flask fitted with a thermometer, a mechanical stirrer, an 8-in. distillation column packed with burl saddles, a Dean-Stark trap, and a reflux condenser. The reaction mixture was heated with stirring to 130° C., during which time the reaction mixture became homogeneous. The mechanical stirrer was removed and boiling chips were added to the reaction flask. The reaction mixture was heated at reflux until 20 ml. of water was removed (7.5 hours). During the reaction period, the reflux temperature climbs from 173° C. to 199° C. A glc analysis of the reaction mixture showed 13% xylene, 16% aniline, 3% hydroquinone, 64% product, and 4% diamine by-product.

Isolation: The reaction flask was fitted with a thermometer, a nitrogen ebullator, a 3-in. packed column and a straight over distillation head. The product distilled over at a pot temperature of 204°-205° C., a heat temperature of 195°-209° C., and a pressure of 4.5 mm. The distillate was poured into a ceramic dish and was allowed to solidify. The distillate weighed 137 g. and assayed 99.2% by glc for a conversion to product of 74%. The distillation residue weighed 22 g. and assayed 23% product and 77% diamine for a conversion to diamine of 6.7%.

The purity of product (p-hydroxydiphenylamine), and the percent hydroquinone (HQ) converted to product and diamine by-product using different catalysts and employing substantially the same procedure as is described in Example 1 are set forth in the following Table, as are the reaction temperatures and times. Each reaction was continued until the theoretical amount of water was removed. In Examples 4 and 5, a 7 mole percent excess of aniline was used, and in the other examples a 30 mole percent was used.

TABLE

| Example | Catalyst | Temp. °C. | Time | Purity, % | % HQ Converted to Product | % HQ Converted to Diamine |
|---|---|---|---|---|---|---|
| 1 | $Al_2(SO_4)_3 \cdot 18H_2O$, 1.9 | 173–199 | 7.50 | 99.2 | 73.4 | 6.7 |
| 2 | $Al_2(SO_4)_3 \cdot 18H_2O$, 3.9 | 171–185 | 5.50 | 97.4 | 75.5 | 4.0 |
| 3 | $Al_2(SO_4)_3 \cdot 18H_2O$, 1.9 | 180–198 | 5.50 | 98.3 | 73.0 | 5.6 |
| 4 | $Al_2(SO_4)_3 \cdot 18H_2O$, 1.9 | 195–212 | 6.50 | 98.6 | 80.0 | 6.4 |
| 5 | $Al(OCOCH_3)_3$, 2.0 | 187–202 | 7.00 | — | 87.0 | 8.5 |
| 6 | Silica-Alumina, 50.0 | 164–234 | 7.75 | 95.3 | 77.3 | 8.7 |
| 7 | Silica-Alumina, 50.0 | 150–212 | 7.50 | 97.6 | 72.5 | 6.3 |
| 8 | $FeCl_3 \cdot 6H_2O$, 2.0 | 188–199 | 8.00 | 96.4 | 67.2 | 7.2 |
| 9 | $FeCl_3$, 2.0 | 191–208 | 4.50 | 97.7 | 66.2 | 9.3 |
| 10 | $Fe_2(SO_4)_3$, 2.0 | 162–168 | 4.50 | — | 22.9 | — |
| 11 | $AlCl_3$, 2.0 | 176–190 | 5.50 | 97.3 | 78.4 | 6.1 |
| 12 | $Al(OCH[CH_3]_2)_3$, 2.0 | 187–207 | 7.75 | 98.9 | 64.5 | 9.1 |
| 13 | $FeCl_3 \cdot 6H_2O$, 0.8 | 190–197 | 14.25 | 97.0 | 69.6 | 6.1 |

The invention has been described in detail with particular reference to certain preferred embodiments thereof, but it will be understood that variations and modifications can be effected within the spirit and scope of the invention.

I claim:

1. Process for the preparation of a p-arylaminophenol having the formula

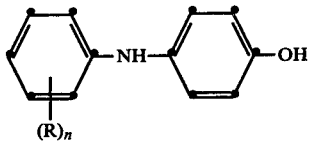

which comprises reacting hydroquinone with a primary arylamine having the formula

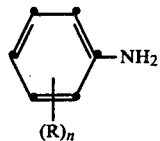

at a temperature of about 170° to 220° C. in the presence of a catalytic amount of aluminum sulfate, or an aluminum lower carboxylate while removing the water of reaction in the form of an azeotrope, wherein R is lower alkyl or lower alkoxy and n is 0, 1 or 2.

2. Process according to claim 1 wherein the catalytic amount is about 0.10 to 0.50 weight percent based on the hydroquinone and calculated as aluminum.

3. Process for the preparation of p-hydroxydiphenylamine which comprises reacting hydroquinone with aniline at a temperature of about 170° to 195° C. in the presence of about 0.12 to 0.30 weight percent, based on the weight of the hydroquinone and calculated as aluminum, of aluminum sulfate or aluminum acetate while removing the water of reaction in the form of an azeotrope.

* * * * *